United States Patent [19]

Dolle et al.

[11] Patent Number: 5,622,967
[45] Date of Patent: Apr. 22, 1997

[54] QUINOLONE CARBOXAMIDE CALPAIN INHIBITORS

[75] Inventors: Roland E. Dolle, King of Prussia; Todd L. Graybill, Pottstown; Irennegbe K. Osifo, West Chester; Alex L. Harris, Lansdale; Matthew S. Miller, Newtown; Jill S. Gregory, Phoenixville, all of Pa.

[73] Assignee: Sterling Winthrop, Inc., New York, N.Y.

[21] Appl. No.: 450,961

[22] Filed: May 25, 1995

Related U.S. Application Data

[62] Division of Ser. No. 54,122, Apr. 26, 1993.

[51] Int. Cl.⁶ ........................ C07D 215/233; A61K 31/47
[52] U.S. Cl. ............................................. 514/312; 546/156
[58] Field of Search .............................. 546/156; 514/312

[56] References Cited

PUBLICATIONS

Wentland, Mark P., "3–Quinolinecarboxamides", J Med Chem, vol. 36, pp. 1580–1596, 1993.

Primary Examiner—C. Warren Ivy
Assistant Examiner—D. Margaret M. Mach
Attorney, Agent, or Firm—William J. Davis; Paul E. Dupont; Imre (Jim) Balogh

[57] ABSTRACT

A compound of the formula

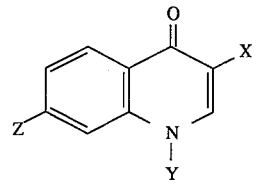

wherein:
Z is aryl, substituted aryl, phenyl-lower-alkyl, hetero-aryl, substituted heteroaryl, heterocycloalkyl, heterocyclocalkyl-lower-alkyl, hetero-aryl-lower-alkyl wherein one or more hydrogens of aryl and heteroaryl is optionally replaced by A and B;
Y is lower cycloalkyl, aryl, phenyl-lower-alkyl, hetero-aryl, heterocycloalkyl, heterocyclocalkyl-lower-alkyl, hetero-aryl-lower-alkyl wherein one or more hydrogens of aryl and heteroaryl is optionally replaced by A and B;
X is $CONH_2$, CONHOH, tetrazole, $SO_2N(R)_2$, $PO(OH)_2$, $CON(R)_2$, or CONR—CHR—CO—A or CONR—$(CHR)_n$—A;
A and B is independently H, OH, OR, halo, $CF_3$, lower alkyl, $N(R)_2$, $CON(R)_2$, SR, $NHSO_2R$, hydroxy-lower-alkyl, NHCOR, $NRSO_2CF_3$, $OSO_2CF_3$, or CN;
R is H, lower-alkyl, phenyl-lower-alkyl, hydroxy-lower-alkyl, CO-lower-alkyl, or CO—$(CH_2)_n$—aryl; and
n is 1, 2, or 3, and a pharmaceutically acceptable salt thereof.

16 Claims, No Drawings

QUINOLONE CARBOXAMIDE CALPAIN INHIBITORS

This application is a division of application Ser. No. 08/054,122, filed on Apr. 26, 1993.

BACKGROUND OF THE INVENTION

1. Field of the Invention

This invention relates to a series of novel non-peptidic quinolone carboxamides which exhibit selective inhibition of Calpain I, to compositions containing the novel non-peptidic quinolone carboxamides and methods for therapeutic use. The Calpain I inhibitors described in this invention possess particular utility in treatment of neurodegenerative diseases.

2. Reported Developments

Calpain is a cytosolic protease enzyme found in all mammalian tissue and cell types. There are two forms of the enzyme with different sensitivities to calcium; the high-sensitivity form, calpain I, is activated by a low calcium concentration (2–75 μM), and the low-sensitivity form, calpain II, is activated by a higher calcium concentration (200–800 μM). Although calpain II is the prominant form, calpain I is concentrated in synapses and neuronal cell bodies and is thought to be involved in the phenomenon of long-term synaptic potentiation.

The location of active calpain explain how calpain can promote: (1) down-regulation of membrane-associated active protein kinase C; (2) formation of a calpain-activated soluble kinase; and (3) reorganization of the cytoskeleton (Melloni, E., and Pontremoli, S. (1989), The Calpains, *Trends Neurosci.* 12, 438–44). Inactivation of the kinase results in repression of superoxide anion production, a process correlated to the protein kinase C-mediated phosphorylation of membrane proteins. Formation of a soluble, fully active kinase, operating in association with active calpain, results in selective modification in the organization of the cytoskeletal proteins, which is correlated with the extracellular discharge of granule contents. These conclusions have been reached by specific and direct inhibition of the proteinases, which results in: (1) a significant increase in superoxide anion production; (2) a marked decrease in the down-regulation of protein kinase C activity; (3) reduced formation of calpain-activated protein kinase; (4) decreased phosphorylation and phosphorylation-mediated proteolytic degradation of cytoskeletal proteins; and (5) inhibition of granule exocytosis.

In addition, studies of (Lee, K. S., Frank, S., Vanderklish, P., Arai, A., and Lynch, G. (1991), Inhibition of Proteolysis Protects Hippocampal Neurons from Ischemia, *Proc. Nat. Acad. Sci. USA*, 88, 7233) suggest that the inhibition of calpain may protect from various ischemia induced-neurodegeneration, essential hypertension, and benefits CNS disorders, and stroke.

A wide variety of peptide analogs are reported to inhibit the action of proteases (Mehdi, Shujaath, Cell-Penetrating Inhibitors of Calpain, *TIPS*, 16, 150 April 1991). These peptidyl analogs include: epoxisuccinates (E-64), leupeptin (CH₃CO-Leu-Leu-ArgH), and ketopeptides. However, these inhibitors suffer from some of the following disadvantages:

weak enzyme specificity,
lack of inhibitory potency,
inhibit wide variety of proteases in addition to calpain I, and
multi-inhibition of various enzymes limits their therapeutic applicability.

A limited number of peptidyl methyl ketone analogs constitute a well-known class of compounds having enzymatic (papain, cathepsin B) inhibition activity. These analogs, however, are essentially devoid of potency and selectivity in inhibiting calpain I.

In spite of various known calpain inhibitors, no effective therapy has yet been developed for the majority of ischemia-induced neurodegenerative diseases, CNS disorders, and stroke. Consequently, there is a need for therapeutic agents effective in the treatment and prevention of these diseases.

SUMMARY OF THE INVENTION

Novel quinolone analogs which are selective calpain inhibitors are provided having the formula (I)

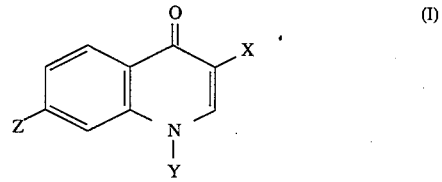

wherein:

Z is aryl, substituted aryl, phenyl-lower-alkyl, hetero-aryl, substituted heteroaryl, heterocycloalkyl, heterocycloalkyl-lower-alkyl, hetero-aryl-lower-alkyl wherein one or more hydrogens of aryl and heteroaryl is optionally replaced by A and B;

Y is lower cycloalkyl, aryl, phenyl-lower-alkyl, hetero-aryl, heterocycloalkyl, heterocyclocalkyl-lower-alkyl, hetero-aryl-lower-alkyl wherein one or more hydrogens of aryl and heteroaryl is optionally replaced by A and B;

X is CONH₂, CONHOH, tetrazole, SO₂N(R)₂, PO(OH)₂, CON(R)₂, or CONR—CHR—CO—A or CONR—(CHR)$_n$—A;

A and B is independently H, OH, OR, halo, CF₃, lower alkyl, N(R)₂, CON(R)₂, SR, NHSO₂R, hydroxy-lower-alkyl, NHCOR, NRSO₂CF₃, OSO₂CF₃, or CN;

R is H, lower-alkyl, phenyl-lower-alkyl, hydroxy-lower-alkyl, CO-lower-alkyl, or CO—(CH₂)$_n$-aryl; and n is 1, 2, or 3, and a pharmaceutically acceptable salt thereof.

Particularly preferred embodiment of this invention are compounds according to formula (II):

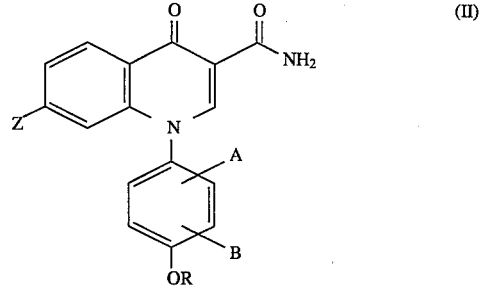

wherein:

Z is aryl, phenyl-lower-alkyl, hetero-aryl, heterocycloalkyl, heterocycloalkyl-lower-alkyl, hetero-aryl-lower-alkyl wherein one or more hydrogens of aryl and heteroaryl is optionally replaced by A and B;

A and B is independently H, OH, OR, halo (Cl, Br, F), CF₃, lower alkyl, or N(R)₂, CON(R)₂, SR, NHSO₂R, hydroxy-lower-alkyl, NHCOR, NRSO₂CF₃, OSO₂CF₃, and CN;

R is H, lower-alkyl, phenyl-lower-alkyl, hydroxy-lower-alkyl, CO-lower-alkyl, or CO—(CH₂)$_n$-aryl; and n is 1,2, or 3, and a pharmaceutically acceptable salt thereof.

As used herein the following terms shall be understood to have the following meanings, unless otherwise indicated.

"Alkyl" means a saturated or an unsaturated aliphatic hydrocarbon which may be either straight- or branched-chain. Preferred groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" means an alkyl group as above, having 1 to 7 carbon atoms. Suitable lower alkyl groups are methyl, ethyl, n-propyl, isopropyl, butyl, tert-butyl, n-pentyl, neopentyl, n-hexyl, and n-heptyl.

"Aryl" means phenyl and substituted phenyl.

"Heteroaryl group" or "heterocyclic group" means, 3, 5, 6 or 7 membered ring having I to 3 hetero atoms which may be nitrogen, oxygen or sulfur, including, pyridyl, pyrimidyl, pyrazolyl, imidazolyl, isoxazolyl, tetrazolyl, furyl, thienyl, oxazolyl, thiazolyl, piperidyl, morpholinyl, imidazolinyl, piperazinyl or thiamorpholinyl.

"Substituted aryl" and "substituted heteroaryl" mean an aryl or heteroaryl group in which one or more of the hydrogens has been replaced by the the same or different substituents including halo, lower lo alkyl, nitro, amino, acylamino, hydroxyl, lower alkoxy, aryl, heteroaryl, lower alkoxy, alkylsulfonyl, trifiuoromethyl, morpholinoethoxy, morpholino-sulfonyl, and carbobenzoxy-methylsulfamoyl.

Pharmaceutically acceptable salts include both acid and base addition salts. Pharmaceutically acceptable acid addition salt refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid, and the like, and organic acids such as acetic acid, propionic acid, glycolic acid, pyrubic acid, fumaric acid, tartaric acid, citric acid, benzoic acid, cinnamic acid, mandelic acid, methanesulfonic acid, and p-toluenesulfonic acid and the like. Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically accceptable organic non-toxic bases include salts of primary, secondary, and tertiary amines, substituted amines including naturally occuring substituted amines, cyclic amines and basic ion exchange resins, such as isopropylamine, tripropylamine, ethanolamine, 2-diethylaminoethanol, 2-dimethylaminoethanol, dicyclohexylamine, lysine, arginine, histidine, caffeine, procain, hydrabamine, choline, betaine, ethylendiamine, glucosamine, methylglucamine, theobromine, purines, peperiziner, piperidine, polyamine resins and the like. Particularly preferred organic non-toxic bases are isopropylamine, diethylamine, ethanol-amine, dicyclohexylamine, choline and caffeine.

This invention also contemplates pharmaceutically acceptable acid-addition salts of the compounds of Formula I and Formula II. It is well known in the pharmacological arts that nontoxic addition salts of pharmacologically active amine compounds do not differ in activities from their free base. All stereoisomers as well as optical isomers related to the novel calpain inhibitory amino acid analogs described herein are also considered to be within the scope of this invention.

The novel quinolone analogs of the present invention are selective calpain inhibitors. More particularly, the novel quinolone analogs of the present invention bind at the active site of the proteolytic enzyme, specifically calpain I.

The present invention further provides pharmaceutical compositions comprised of the above-described novel quinolone analog inhibitors and method of treating ischemia-induced neurodegenerative diseases, stroke, myocardial infarction, CNS disorders, and immunological diseases involving interleukin 1.

DETAILED DESCRIPTION OF THE INVENTION

The compounds of the present invention are prepared by the general synthetic methods described in Schemes 1 and 2 while the preparation of aniline building blocks are made according to Schemes 3 and 4.

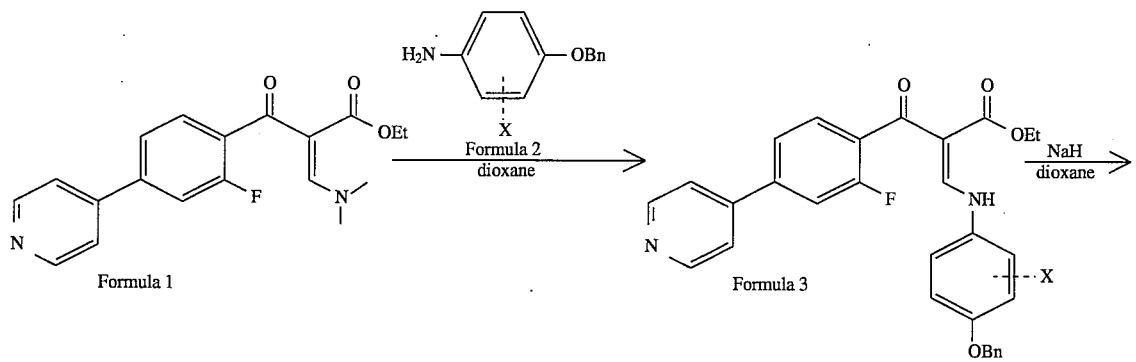

Scheme 1: General Synthetic Scheme For Example 1 and its Analogs

-continued
Scheme 1: General Synthetic Scheme For Example 1 and its Analogs
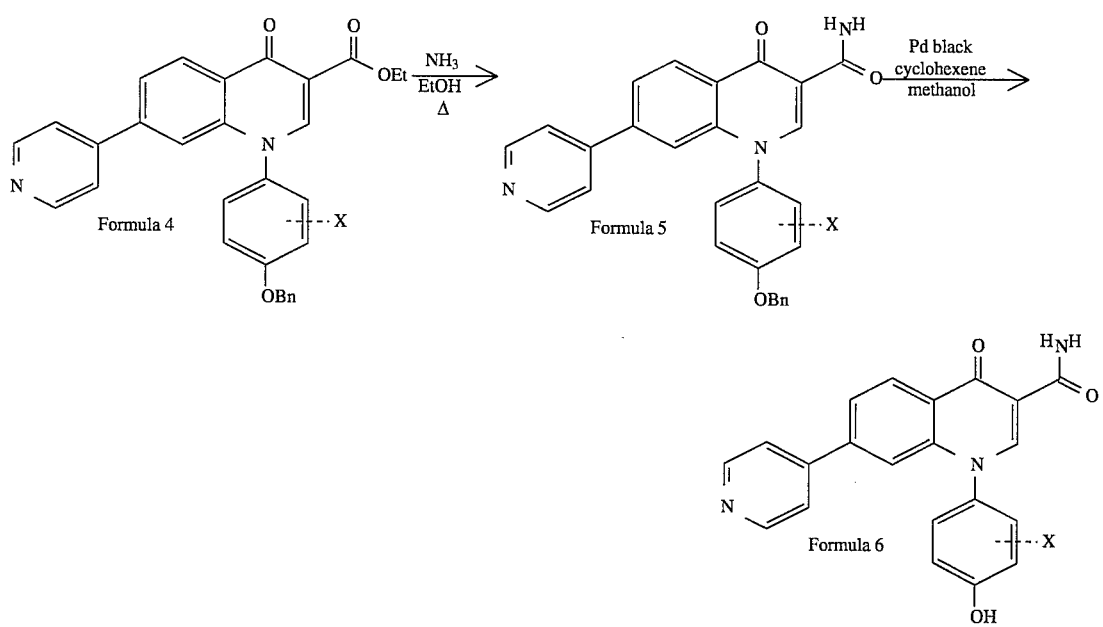
wherein X is as described above for Formulae I and II.
Scheme 2: General Synthetic Scheme For Example 8 and its Analogs
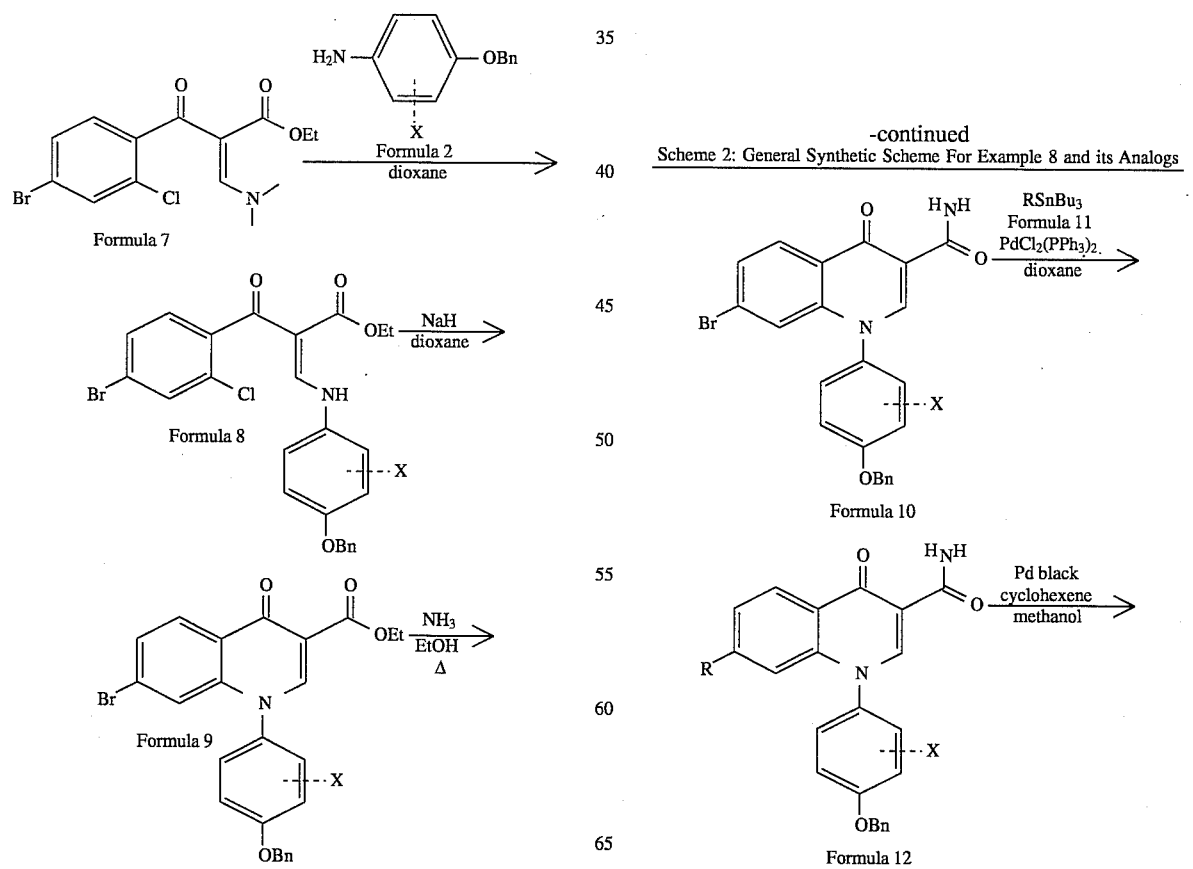

-continued
Scheme 2: General Synthetic Scheme For Example 8 and its Analogs

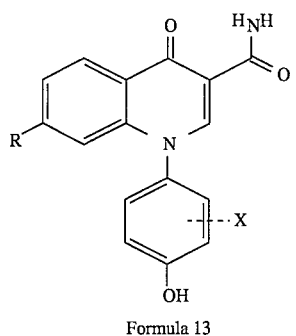

Formula 13 wherein X is as described above for Formulae I and II.

Scheme 3: Preparation of Aniline Building Blocks

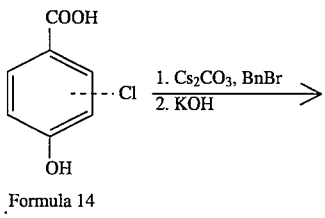

Formula 14

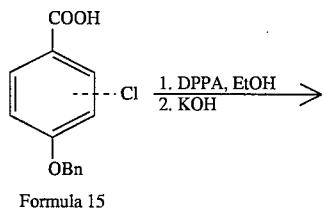

Formula 15

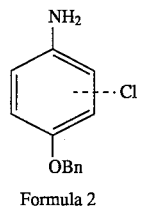

Formula 2

Scheme 4: Preparation of Aniline Building Blocks

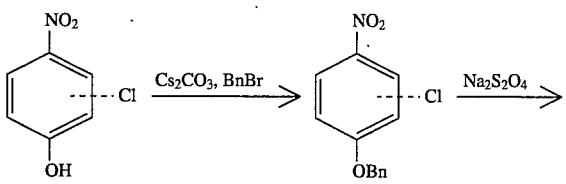

Formula 16      Formula 17

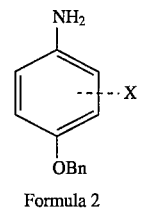

Formula 2 wherein X is as described above for Formulae I and II.

The compounds of the present invention may be prepared by the above-shown synthetic schemes.

Novel quinolones (see Examples 1, 2, 3, 4, 5, 6 and 7) of this invention may be prepared by a mild ring closure reaction of ethyl 2-[4-(4-pyridyl)-2-fluoro-benzoyl]-3-phenylamino-propenoate (Formula 3) with sodium hydride in dioxane followed by treatment of the propeonate with ammonia to afford the desired 1,4-dihydro-1-phenyl-7-(4-pyridyl)-4-oxo-3-quinolinecarboxamide (Formula 5) as shown in Scheme 1.

The ethyl ester (Formula 4) is readily hydrolyzed to the corresponding carboxylic acid which in turn is converted to various novel amides of Formula I and II via the corresponding acid chlorides.

When 4-hydroxyphenyl substitution is desired in 1-position (Formula 6), it is convenient to carry out the hydrogenolysis of benzyloxyphenyl derivative (Formula 5) using palladium black in methanol or cyclohexene.

When 4- amino or 4-acylaminophenyl substitution is desired in 1-position, it is convenient to carry out the hydrogenation of an appropriate 1-(4-nitrophenyl)-quinolone using Pd/C in methanol to yield the desired amine which in turn is converted to various acetylamides as well as sulfonamides.

An alternative method of preparing the compounds of this invention is outlined in Scheme 2. The reaction of 7-bromo compound of the Formula 10 with a heteroaryl tributylstannane in the presence of dichlorobis(triphenylphosphine)palladium provides various novel 7-heteroaryl substituted-quinolones (Examples 8, 9, 10, 11, 12 and 13). Special advantages of this process include the preparations of novel 7-(3-pyrazolyl) (Example 13), 7-(2-chloro-4-pyridyl)(Example 11), 7-(3,6-dichloro4-pyridazinyl) and 7-(4-pyridazinyl) (Example 12) quinolone-3-carboxamides by reactions of 7-bromo compounds of Formula 10 with new heteroaryl tributylstannane agents, 3-pyrazolyl tributylstannane, 2-chloro-4-pyridyl tributylstannane, and 3,6-dichloro-4-pyridazinyl tributylstannane, respectively.

Aniline Building Blocks

The functionalized anilines were prepared according to Scheme 3 and Scheme 4.

Anilines prepared for use in Examples 8, 9, 10, 11, 12 and 13 prepared according to Scheme 3 are as follows:

(a) Preparation of 4-benzyloxy-2-chloroaniline

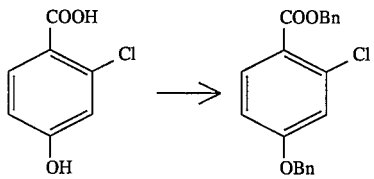

Benzyl bromide (275 mmol, 33 mL) was added to a 350 mL DMF solution of 2-chloro-4-hydroxybenzoic acid (145 mmol, 25.0 g) and $Cs_2CO_3$ (217 mmol, 70.7 g). The mixture was then heated overnight at 75° C. DMF and benzyl bromide were then evaporated under reduced pressure. The residue was then dissolved in 1 L of EtOAc. The EtOAc layer was then washed with water (3×500 mL), 5% $NaHCO_3$ (2×500 mL), brine and then dried over $MgSO_4$. The desired benzyl ester was obtained as a white solid (39 g, 82%), following silica gel chromatography purification (39-50% EtOAc/Hex). $^1H$ NMR (300 MHz, $CDCl_3$) δ:7.82 (d, J=8.8 Hz, 1 H), 7.4 (m, 10 H), 7.06 (d, J=2.1 Hz, 1 H), 6.88 (dd, J=8.8, 2.1 Hz), 5.32 (s, 2 H), 5.09 (s, 2 H).

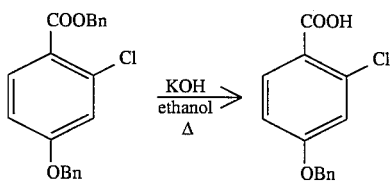

KOH (1.2 mole, 67 g) in 350 mL water was added into a stirred solution of benzylester (120 retool, 39.3 g) in 600 mL absolute ethanol. The solution was then refluxed at 88° C. for 2 hours. The excess ethanol was evaporated under reduced pressure. Water (250 mL) was then added followed by acidification to pH4 with conc. HCl. The precipitate was then filtered, washed with water, and dried overnight in a vacuum oven (60° C./20 mm Hg). 4-Benzyloxy-2-chlorobenzoic acid (30.5 g, 97%) was obtained as a light yellow solid. $^1$H NMR (300 MHz, CDCl$_3$) δ:8.05 (d, J=8.8 Hz, 1 H), 7.4 (m, 5 H), 7.10 (d, J=2.3 Hz, 1 H), 6.93 (dd, J=8.8, 2.5 Hz, 1 H), 5.12 (s, 2 H).

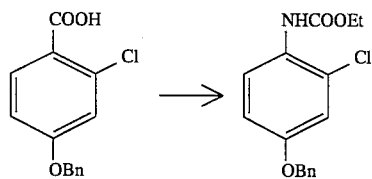

TEA (109 mmol, 15.2 mL) was added by syringe to a suspension of 4-benzyloxy-2-chlorobenzoic acid (28.7 g, 109 mmol) and diphenylphosphoryl azide (DPPA, 109 mmol, 23.5 mL) in 300 mL of toluene. The reaction is exothermic and becomes homogeneous. Ethanol (100 mL) is then added and the solution heated at 105° C. for 2 hr. The cooled solution was then partitioned between water and EtOAc. The aqueous phase was washed with water (200 mL), 0.2N HCl (200 mL), 5% NaHCO$_3$ (200 mL), brine then dried over Na$_2$SO$_4$. Evaporation of solvents produced an orange oil. Silica gel purification (20:10:70 DCM/EtOAc/hex) followed by crystallization from hot hexane, provided the carbamate (27 g, 81%) as a white crystalline solid. $^1$H NMR (300 MHz, CDCl$_3$) δ:8.0 (br s, 1 H), 7.36 (m, 5 H), 6.98 (d, J=2.0 Hz, 1 H), 6.88 (m, 2 H), 4.99 (s, 2 H), 4.22 (q, J=7.2 Hz, 2 H), 1.32 (t, J=7.2 Hz, 3 H).

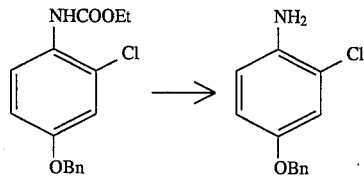

A 20 mL aqueous solution of KOH (49 mmol, 2.75 g) was added to a 100 mL flask containing the carbamate in 25 mL of EtOH. The reaction temperature was then raised to 85° C. for 5 hr. EtOH was then removed under reduced pressure. The residue was partitioned between EtOAc and water. The EtOAc phase was then dried over MgSO$_4$, filtered and then solvents were evaporated to yield the desired 4-benzyloxy-2-chloroaniline as a clear oil (2.17 g, 95%) of excellent purity. $^1$H NMR (300 MHz, CDCl$_3$) δ:7.36–7.45 (m, 5 H), 6.96 (d, J=2.5 Hz, 1 H), 6.71–6.8 (dd, J=8.7, 2.5 Hz, 2 H), 5.0 (s, 2 H).

Aniline prepared for use in Example 3:

(b) Preparation of 4-benzyloxy-3-chloroaniline

The 4-benzyloxy-3-chloroaniline was prepared from 3-chloro-4hydroxybenzoic acid using the same procedure described for the preparation of 4-benzyloxy-2-chloroaniline (Scheme 3). $^1$H NMR (300 MHz, CDCl$_3$) δ:7.35 (m, 5 H), 6.77 (d, J=8.9 Hz, 1 H), 6.72 (d, J=2.1 Hz, 1 H), 6.49 (dd, J=8.9, 2.1 Hz, 1 H), 5.2 (s, 2 H), 3.55 (br s, 2 H).

Aniline prepared for use in Example 6:

(c) Preparation of 4-benzyloxy-2-methylaniline

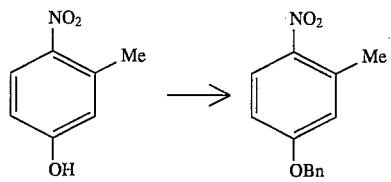

Benzyl bromide (19.6 mmol, 3.4 g) was added dropwise to a slurry of 4-hydroxy-2-methylnitrobenzene (19.6 mmol, 3.0 g), Cs2CO3 (9.8 mmol, 3.2 g) and KI (1 mmol, 0.17 g) in 100 mL of DMF. The reaction was then partitioned between water and EtOAc. The organic phase was then washed with water (3×), 5% K$_2$CO$_3$ solution (2×), brine then dried over MgSO$_4$. Following flash chromatography (5% EtOAc/hexane), white crystals of benzyl ether (2.4 g, 51%) were obtained from EtOAc/Hex. $^1$H NMR (300 MHz, CDCl$_3$) δ:8.11 (d, J=8.9 Hz, 1 H), 7.45 (m, 5 H), 6.88 (m, 2 H), 5.12 (s, 2 H), 2.62 (s, 3 H).

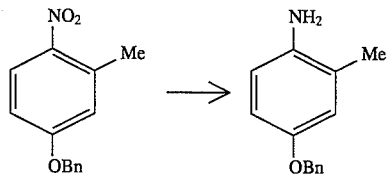

A solution of 4-benzyloxy-2-methyl nitrobenzene (6.4 mmol, 1.5 g) and sodium hydrosulfite (16 mmol, 2.2 g) in 140 mL of MeOH/water (2:1) was refluxed for two hours. Upon cooling, the solution was poured into 500 mL of aqueous ammonia and the product extracted into CH$_2$Cl$_2$ (4×). The organic layer was washed with water, brine and dried over Na$_2$SO$_4$, filtered and concentrated to provide 4-benzyloxy-2-methylaniline (0.47 g, 51%) as a light brown oil. $^1$H NMR (300 MHz, CDCl$_3$) δ:7.4 (m, 5 H), 6.76 (d, J=2.1 Hz, 1 H), 6.70 (dd, J=7.2, 2.1 Hz, 1 H), 6.61 (d, J=7.2 Hz, 1 H), 4.98 (s, 2 H), 2.15 (s, 3 H).

Aniline prepared for use in Example 4:

(d) Preparation of 4-benzyloxy-2-fluoroaniline

The 4-benzyloxy-2-fluoroaniline was prepared from 2-fluoro-4-hydroxynitrobenzene using the same procedure described for the preparation of 4-benzyloxy-2-methylaniline (Scheme 4). $^1$H NMR (300 MHz, CDCl$_3$) δ:7.35 (m, 5 H), 6.65 (m, 3 H), 4.95 (s, 2 H), 3.38 (br s, 2 H).

Aniline prepared for use in Example 5:

(e) Preparation of 4-benzyloxy-3-fluoroaniline

The 4-benzyloxy-3-fluoroaniline was prepared from 3-fluoro-4-hydroxynitrobenzene using the same procedure described for the preparation of 4-benzyloxy-2-methylaniline (Scheme 4). $^1$H NMR (300 MHz, CDCl$_3$) δ:7.35 (m, 5 H), 7.79 (t, J=9.4 Hz, 1 H), 6.44 (dd, J=13.0, 2.1 Hz, 1 H), 6.31 (ddd, J=9.4, 2.5, 2.1 Hz, 1 H), 3.50 (br s, 2 H).

Aniline prepared for use in Example 7:

(f) Preparation of 4-benzyloxy-2-trifluoromethylaniline

The 4-benzyloxy-2-trifluoromethylaniline was prepared from 2-trifluoromethyl-4-hydroxynitrobenzene using the same procedure described for the preparation of 4-benzyloxy-2-methylaniline (Scheme 4). $^1$H NMR (300 MHz, CDCl$_3$) δ:7.35 (m, 5 H), 7.08 (d, J=2.2 Hz, 1 H), 6.95 (dd, J=8.7, 2.2 Hz, 1 H), 6.65 (d, J=8.7 Hz, 1 H), 4.98 (s, 2 H), 3.85 (br s, H).

Stannanes of Formula 11 for use in the Examples were prepared as follows:

(g) Preparation of 3-pyrazole tributylstannane

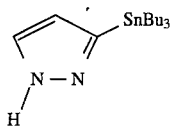

A freshly prepared solution of diazomethane in ether (~10 mmol, approx. 0.3 M prepared from "Diazald" (Aldrich) according to the suppliers directions) was carefully added to a 200 mL flask (with "clear seal" joint) containing ethynyl tributyl stannane in 50 mL of THF. The solution was stirred at RT overnight. Unreacted diazomethane was recovered using a stream of N$_2$ and then reduced pressure. The desired 3-pyrazole tributyl stannane was obtained as a clear oil (0.66 g, 29%) following silica gel chromatography (2% MeOH/DCM). $^1$H NMR (300 MHz, CDCl$_3$) δ:7.72 (d, J=1.6 Hz, 1 H), 6.40 (d, J=1.6 Hz, 1 H), 1.55 (m, 6H), 1.11 (t, J=8.1 Hz, 6H), 0.897 (t, J=7.3 Hz, 9 H).

(h) Preparation of 3-pyridyl tributylstannane

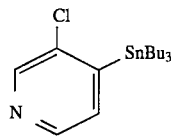

A solution of 3-chloropyridine in 2 mL of THF was added dropwise by syringe into a −85° C. solution of LDA (10.5 mmol) in 8 mL of THF.

The reaction was then stirred for 30 min and then tributyltin chloride (10.5 mmol, 2.8 mL) was added at −78° C. The temperature was allowed to warm slowly overnight. Following evaporation of solvents, purification by silica gel chromatography provided the 3-pyridyl tributylstannane (6.7 mmol, 64%) as a clear colorless oil. $^1$H NMR (300 MHz, CDCl$_3$) δ:8.49 (s, 1 H), 8.36 (d, J=4.6 Hz, 1 H), 7.31 (d, J=4.6 Hz, 1 H), 1.63 (m, 6 H), 1.32 (m, 6 H), 1.18 (m, 6 H), 0.89 (t, J=7.2 Hz, 9 H).

(i) preparation of 3,6-dichloropyridazine tributylstannane

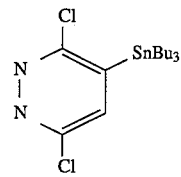

A THF solution (10 mL) of 3,6-dichloropyridazine (16.8 mmol, 2.5 g) was added dropwise to a solution of lithium tetramethylpiperidine (20.1 mmol) in 170 mL of THF at −78° C. After one hour at −78° C., tributyltin chloride (21.8 mmol, 5.8 mL) was added to the anion solution and the solution was allowed to warm slowly overnight.

Following evaporation of solvents, purification by silica gel chromatography (30% EtOAc/Hexane) provided the stannane (0.56 g) as a light yellow oil. $^1$H NMR (300 MHz, CDCl$_3$) δ:7.47 (s, 1 H), 1.52 (m, 6 H), 1.32 (m, 6 H), 1.28 (m, 6 H), 0.91 (t, J=7.3 Hz, 9 H).

The following examples will furhter illustrate the preparation of the compounds of the present invention.

EXAMPLE 1

1,4-Dihydro-1-(4-hydroxyphenyl)-4-oxo-7-(4-pyridinyl)=3-quinolinecarboxamide

The synthesis of the title compound was accomplished according to Scheme 1 and utilized the commercially available 4-benzyloxyaniline of Formula 2.

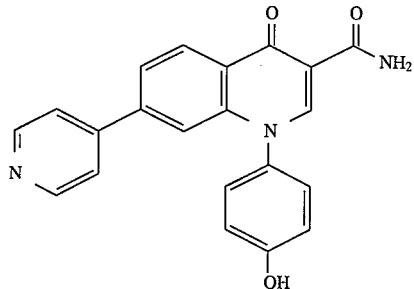

C, H, N calculated for C$_{21}$H$_{15}$N$_3$O$_3$.CH$_3$SO$_3$H. ½ H$_2$O: calc.: % C=57.14; % H=4.36; % N=9.07.
found: % C=56.82; % H=4.35; % N=8.85.

EXAMPLE 2

1,4,Dihydro-1-(3,4-dihydroxyphenyl)-4-oxo-7-(4-pyridinyl),3-quinolinecarboxamide

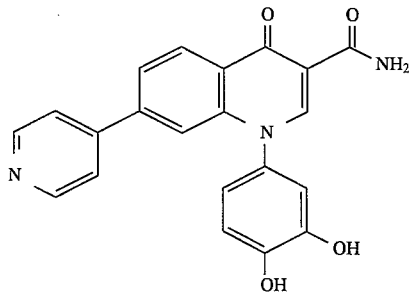

Preparation of the title compound is outlined in Scheme 1 and utilized commercially available 3,4-dimethoxyaniline. The phenol deprotection step was accomplished using excess $BBr_3$ in refluxing methylene chloride in place of the hydrogenolysis step. $^1$H NMR (300 MHz, DMSO) 9.12 (br s,1 H), 8.82 (br s, 2 H), 8.56 (s, 1 H), 8.51 (d, J=8.5 Hz, 1 H), 7.98 (m, 3 H), 7.65 (m, 1 H), 7.42 (s, 1 H), 6.90 (m, 3 H). Exact Mass (m/z) calcd. for $C_{21}H_{16}N_3O_4$: 374.1140 found: 374.1146.

EXAMPLE 3

1,4-Dihydro-1-(3-chloro-4-hydroxyphenyl)-4-oxo-7-(4-pyridinyl)-3-quinolinecarboxamide

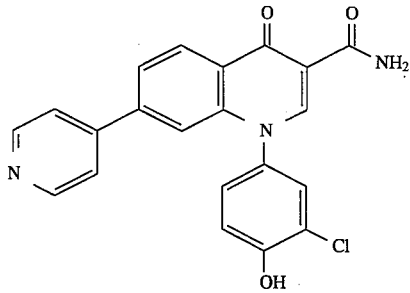

The title compound was prepared according to Scheme 1. The requisite 4-benzyloxy-3-chloroaniline (Formula 2) was prepared from commercially available 3-chloro-4-hydroxybenzoic acid.

C, H, N, calculated for $C_{21}H_{14}ClN_3O_3$. 0.66 $H_2O$:
calc.: % C=62.48; % H=3.82; % N=10.41.
found: % C=62.60; % H=3.59; % N=10.11.

EXAMPLE 4

1,4-Dihydro-1-(2-fluoro-4-hydroxyphenyl)-4-oxo-7-(4-pyridinyl)-3-quinolinecarboxamide

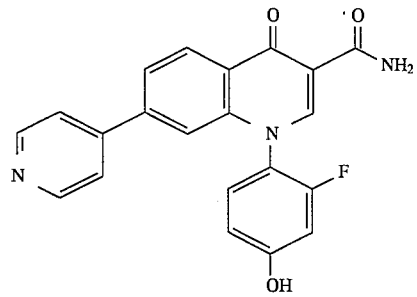

The title compound was prepared according to Scheme 1. The requisite 4-benzyloxy-2-fluoro aniline (Formula 2) was prepared from commercially available 2-fluoro-4-hydroxy nitrobenzene.

C, H, N calculated for $C_{21}H_{14}FN_3O_3$. 0.25 $H_2O$.
calc.: % C=66.40; % H=3.85; % N=11.06.
found: % C=66.20; % H=3.65; % N=11.00.

EXAMPLE 5

1,4-Dihydro-1-(3-fluoro-4-hydroxyphenyl)-4-oxo-7-(4-pyridinyl)-3-quinolinecarboxamide

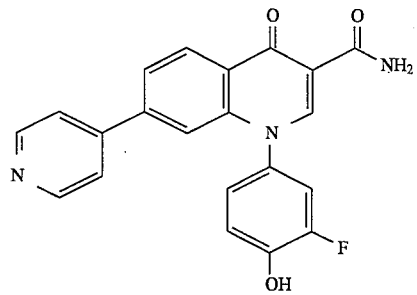

The title compound was prepared according to Scheme 1. The requisite 4-benzyloxy-3-fluoro aniline (Formula 2) was prepared from commercially available 3-fluoro-4-hydroxynitrobenzene.

C, H, N calculated for $C_{21}H_{14}FN_3O_3$. 0.7$H_2O$:
calc.: % C=65.01; % H=4.00; % N=10.83.
found: % C=65.32; % H=3.91; % N=10.45.

EXAMPLE 6

1,4-Dihydro-1-(2-methyl-4-hydroxyphenyl)-4-oxo-7-(4-pyridinyl)-3-quinolinecarboxamide The title compound was prepared according to Scheme 1. The preparation of the enamine starting material (Formula 1) has been described in U.S. Pat. No. 4,959,363. The synthesis of 4-benzyloxy-2-methyl aniline is shown in Scheme 4.

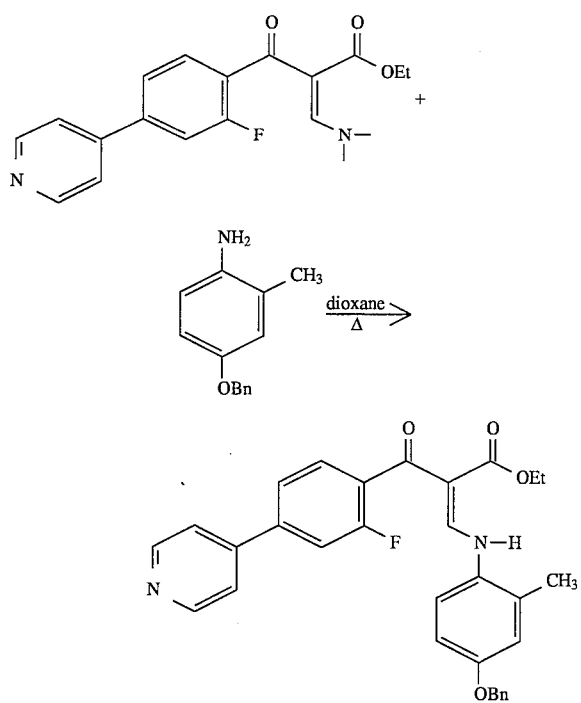

A solution of enamine (0.87 mmol, 300 mg) and 4-benzyloxy-2-methylaniline (1.3 mmol, 189 mg) in 20 mL dioxane was heated at reflux for 6 hours then allowed to cool. Following evaporation of solvents, silica gel chromatography provided the desired adduct (364 mg, 82%) as a bright yellow oil. $^1$H NMR (300 MHz, CDCl$_3$) ~3:1 mixture of E/Z isomers. Major isomer δ:8.66 (d, J=4.8 Hz, 2 H), 8.52 (d, J=13.3 Hz, 1 H), 7.6–7.2 (m, 12 H), 6.88 (m, 2 H), 5.05 (s, 2 H), 4.08 (q, J=7.1 Hz, 2 H), 2.40(s, 3 H), 1.05 (t, J=7.1 Hz, 3 H).

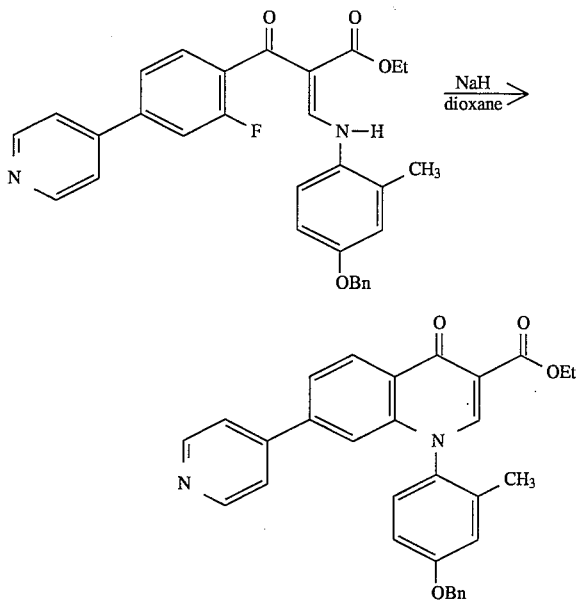

Sodium hydride (1.8 mmol, 44 mg) was added to a solution of enamine (0.71 mmol, 364 mg) in 30 mL dioxane. The solution was then heated at 70° C. until complete consumption of enamine. Upon completion of the reaction, the dioxane was evaporated under reduced pressure. The residue was then partitioned between water and EtOAc. The organic layer was then washed with water (2 ×), brine and dried over Na$_2$SO$_4$. The desired quinolone (322 mg, 92%) was obtained as a light yellow crystalline solid following recrystallization from warm EtOAc. $^1$H NMR (300 MHz, CDCl$_3$) δ:8.68 (d, J=5.5 Hz, 2 H), 8.48 (s, 1 H), 7.68 (d, J=6.1 Hz, 1 H), 7.5–7.2 (m, 10 H), 7.05 (m, 3 H), 5.18 (s, 2 H), 4.43 (q, J=7.1 Hz, 2 H), 2.08 (s, 3 H), 1.46 (t, J=7.2 Hz, 3 H).

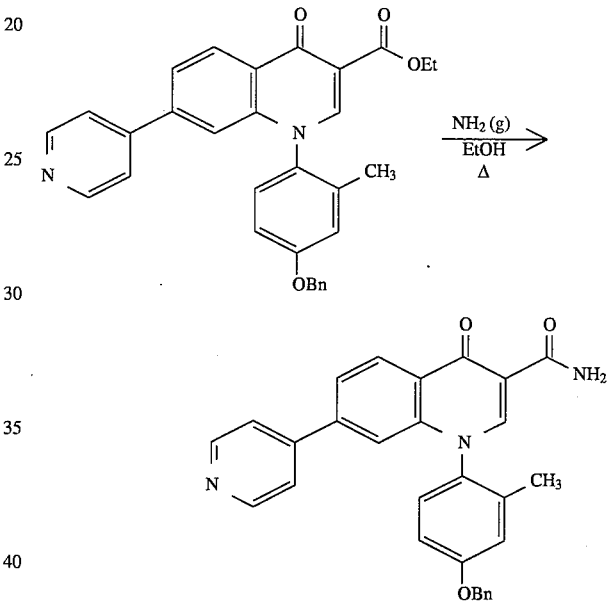

Cold EtOH saturated with ammonia (100 mL) was added to a stainless steel bomb containing the ester (0.66 mmol, 322 mg). The bomb was sealed and heated at 120° C. for 15 hours and then allowed to cool. The ethanol was then evaporated and the residue chromatographed on silica gel (5% MeOH/CH$_2$Cl$_2$). Purification in this manner provided the quinolone amide as a white crystalline solid following evaporation of solvents (181 mg, 60%). $^1$H NMR (300 MHz, CDCl$_3$) δ:9.77 (d, J=5.1 Hz, 1 H), 8.82 (s, 1 H), 8.71 (m, 3 H), 7.78 (d, J=8.3 Hz, 1 H), 7.48 (m, 4 H), 7.27 (m, 2 H), 7.13 (d, J=1.2 Hz, 1 H), 7.07 (m, 2 H), 5.90 (d, J=5.1 Hz, 1 H), 5.20 (s, 2 H), 2.03 (s, 3 H).

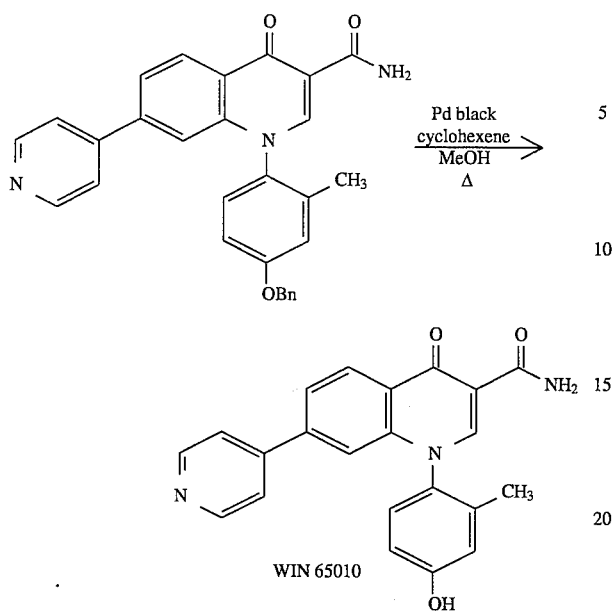

A solution of benzyl ether (0.39 mmol, 180 mg), palladium black (41 mg) and cyclohexene (2 mL) in 20 mL of methanol was refluxed for 2.5 h then passed (while hot) through a pad of celite to remove Pd catalyst. Crystallization from ethanol provided the title compound (91 mg, 63%) as a white solid.

C, H, N calculated for $C_{22}H_{17}N_3O_3 \cdot 0.25\ H_2O$:
calc.: % C=70.23; % H=4.69; % N=11.18.
found: % C=70.01; % H=4.57; % N=10.89.

EXAMPLE 7

1,4-Dihydro-1-(2-trifluoromethyl-4-hydroxyphenyl)-4-oxo-7-(4-pyridinyl)-3-quinolinecarboxamide

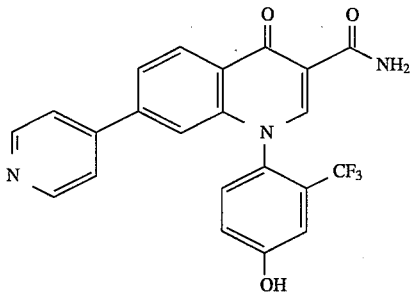

The title compound was also prepared according to Scheme 1. The requisite 4-benzyloxy-2-trifluoromethyl nitrobenzene was prepared described in Scheme 4.

C, H, N calculated for $C_{22}H_{14}F_3N_3O_3 \cdot 1.4\ H_2O$:
calc. % C=58.64; % H=3.76; % N=9.33.
found % C=58.47; % H=3.39; % N=9.27.

EXAMPLE 8

1,4-Dihydro-1-(2-chloro-4-hydroxyphenyl)-4-oxo-7-(4-pyridinyl)-3-quinolinecarboxamide

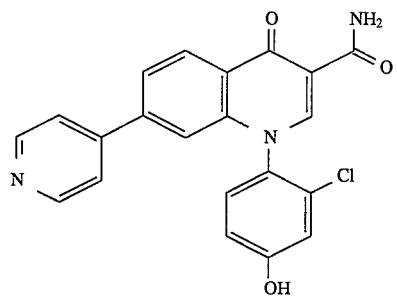

The title compound was prepared according to Scheme 2. 4-Pyridinyl tributylstannane (Formula 11) was obtained following the method described in U.S. Pat. No. 4,959,363.

C, H, N calculated for $C_{21}H_{14}ClN_3O_3 \cdot \tfrac{2}{3}\ H_2O$.
calc.: % C=62.53; % H=3.80; % N=10.42.
found: % C=62.42; % H=3.43; % N=10.04.

EXAMPLE 9

1,4-Dihydro-1-(2-chloro-4-hydroxyphenyl)-4-oxo-7-(3-pyridinyl)-3-quinolinecarboxamide

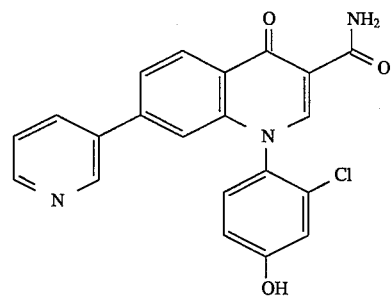

The title compound was prepared according to Scheme 2. 3-Pyridinyl tributyl stannane (Formula 11) was obtained according to Mitchell, T.N., Organic Magnetic Resonance, 7, 610 (1975).

C, H, N calculated for $C_{21}H_{14}ClN_3O_3 \cdot 0.25\ H_2O$.
calc.: % C=63.64; % H=3.69; % N=10.60.
found: % C=63.85; % H=3.51; % N=10.35.

EXAMPLE 10

1,4-Dihydro-1-(2-chloro-4-hydroxyphenyl)-4-oxo-7-(3-furyl)-3-quinolinecarboxamide

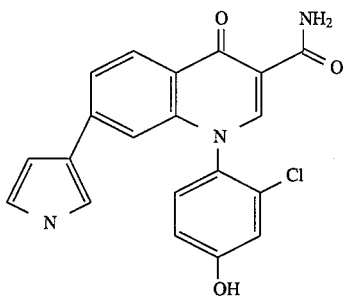

The title compound was prepared according to Scheme 2. 3-Stannyl furan (Formula 11) was prepared as published by Fleming, I. and Taddei M., Synthesis, 898–899 (1985). $^1$H NMR (300 MHz, DMSO) δ:9.16 (d, J=4.2 Hz, 2 H), 8.44 (s, 1 H), 8.32 (d, J=8.4 Hz, 1 H), 8.26 (s, 1 H), 7.77 (dd, J=8.4, 1.5 Hz, 1 H), 7.73 (t, J=1.7 Hz, 1 H), 7.61 (d, J=8.8 Hz, H), 7.12 (d, J=2.6 Hz, 1 H), 6.98 (dd, J=8.7, 2.6 Hz, 1 H), 6.91 (d, J=1.4 Hz, 1 H), 6.77 (d, J=2.3 Hz 1 H). FAB Mass Spec: m/z=381 for [M]$^+$.

EXAMPLE 11

1,4-Dihydro-1-(2-chloro-4-hydroxyphenyl)-4-oxo-7-(2-chloro-4-pyridinyl)-3-quinolinecarboxamide

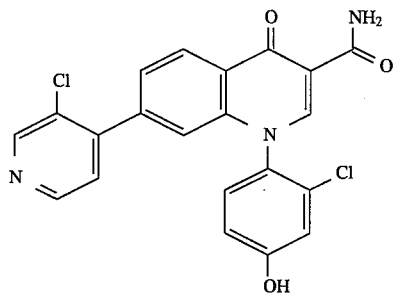

The title compound was synthesized according to Scheme 2. $^1$H NMR (300 MHz DMSO) 67 :9.15 (d, J=3.5 Hz, 1 H), 8.73 (s, 1 H), 8.59 (d, J=4.8 Hz, 1 H), 8.57 (s, 1 H), 8.49 (d, J=8.2 Hz, 1 H), 7.68 (m, 3 H), 7.47 (d, J=4.9 Hz, 1 H), 7.13 (s, 1 H), 7.04 (s, 1 H), 6.97 (d, J=8.8 Hz, 1 H). Mass spectra: m/z=426 for [M]$^+$.

EXAMPLE 12

1,4-Dihydro-1-(2-chloro-4-hydroxyphenyl)-4-oxo-7-(4-pyridazinyl)-3-quinolinecarboxamide

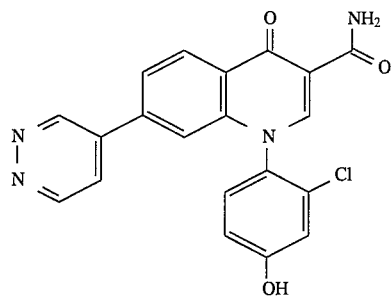

The title compound was prepared according to Scheme 2. $^1$H NMR (300 MHz, DMSO) 67 :9.52 (dd, J=5.5, 1.1 Hz, 1 H), 9.30 (dd, J=5.5, 1.1 Hz, 1. H), 9.13 (d, J=4.1 Hz, 1 H), 8.55 (s, 1 H), 8.53 (d, J=8.4 Hz, 1 H), 8.03 (dd, J=8.4, 1.6 Hz, 1 H), 7.89 (dd, J=5.5, 2.4 Hz, 1 H), 7.72 (d, J=4.4 Hz, 1 H), 7.65 (d, J=8.7 Hz, 1 H), 7.30 (d, J=1.4 Hz, 1 H), 7.12 (d, J=2.3 Hz, 1 H), 6.97 (dd, J=8.6, 2.8 Hz, 1 H). FAB MS spectra: m/z=393.1 [M+H]$^+$.

EXAMPLE 13

1,4-Dihydro-1-(2-chloro-4-hydroxyphenyl)-4-oxo-7-(3-pyrazolyl)-3-quinolinecarboxamide The title compound was prepared according to Scheme 2.

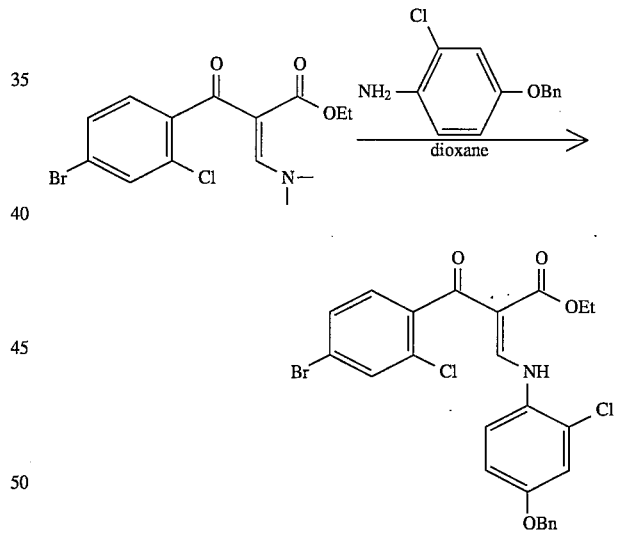

A solution of enamine (14.1 mmol, 5.1 g) and 4-benzyloxy-2chloroaniline (17.5 mmol, 4.1 g) in 40 mL of dry dioxane was heated at 100° C. for 7 hours. t-Butanol (100 mL) was then added and the solution refluxed for an additional 48 h. Solvents were evaporated under reduced pressure. The desired adduct (7.2 g, 90%) was obtained as a crystalline yellow solid following recrystallization (Et$_2$O/hex). $^1$H NMR (300 MHz, CDCl$_3$) δ:8.56 (d, J=13.4 Hz, 1

H), 7.54 (d, J=1.8 Hz, 1 H), 7.45 (dd, J=9.1, 1.8 Hz, 1 H), 7.43 (m, 5 H), 7.38 (d, J=9.1 Hz, 1 H), 7.17 (d, J=8.2 Hz, 1 H), 7.12 (d, J=2.8 Hz, 1 H), 7.00 (dd J=2.8, 2.6 Hz, 1 H), 5.08 (s, 2 H).

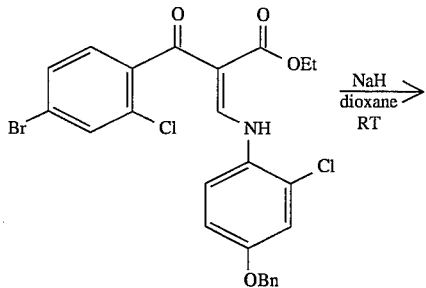

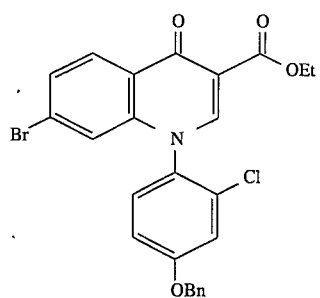

NaH (30.2 mmol, 0.73 g) was added to a solution of enamine (21.5 mmol, 12.1 g) in 400 mL of anhydrous dioxane. The reaction was then allowed to stir for 48 h at RT.

The reaction was quenched with acetic acid (15.1 mmol, 0.86 mL) and stirred an additional 10 min. Baseline impurities were removed by passing the crude reaction mixture through a short plug of silica gel. Evaporation of solvents under reduced pressure followed by crystallization from Et$_2$O/hex provided the quinolone (6.0 g) as a pale yellow solid. An additional 2.7 g of quinolone was obtained by chromatography of the mother liquors. $^1$H NMR (300 MHz, CDCl$_3$)δ: 8.40 (d, J=8.7 Hz, 1 H), 8.34 (s, 1 H), 7.6–7.2 (m, 8 H), 7.11 (dd, J=8.8, 2.7 Hz, 1 H), 6.94 (d, J=1.6 Hz, 1 H), 5.18 (s, 2 H), 4.39 (q, J=7.1 Hz, 2 H), 1.40 (t, J=7.1 Hz, 3 H).

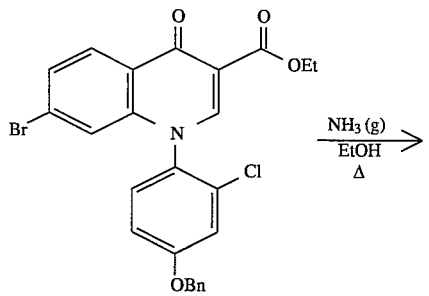

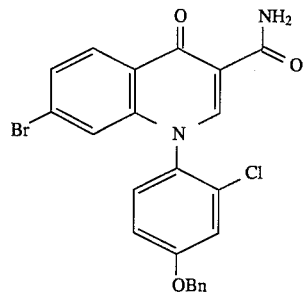

Ethanol (150 mL) saturated with NH$_3$ (g) at 0° C. was quickly added to a stainless steel bomb containing the quinolone ester (2.0 mmol, 1.02 g). The bomb was heated at 150° C. for 20 hrs then allowed to cool slowly to induce crystallization of the amide product from ethanol. The amide was collected on a filter, washed with cold ethanol and dried under high vacuum to yield 0.83 g (86%) of a pale yellow crystalline solid. $^1$H NMR (300 MHz, CDCl$_3$) δ:9.61 (d, J=4.8 Hz, $^1$ H), 8.67 (s, 1 H), 8.41 (d, J=8.7 Hz, 1 H), 7.60 (dd, J=8.7, 1.6 Hz, 1 H), 7.5–7.4 (m, 6 H), 7.36 (d, J=8.8 Hz, H), 7.10 (dd, J=8.8, 2.7 Hz, 1 H), 7.03 (d, J=1.6 Hz, 1 H), 5.75 (d, J=4.1 Hz, 1 H), 5.18 (s, 2 H).

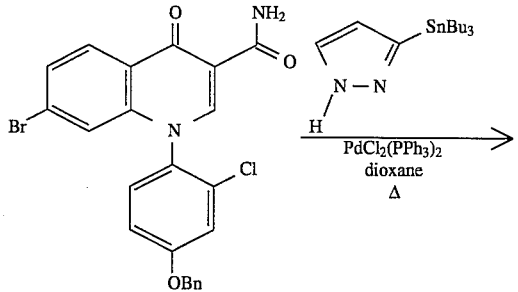

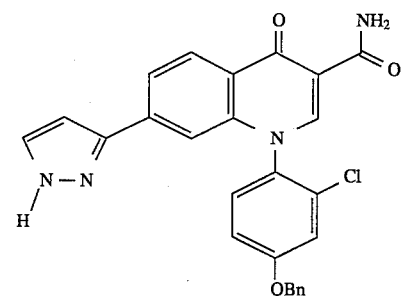

A solution of bromide (0.41 mmol, 200 mg), 3-pyrazoletributylstannane (0.54 mmol, 192 mg) and PdCl$_2$(PPh$_3$)$_2$ (0.041 mmol, 29 mg) in 10 mL dioxane was heated at 125° C. for 30 min. The black solution was then passed directly through a short column of silica gel using 5% MeOH/DCM. Following evaporation of solvents, the desired quinolone (176 mg, 90%) was obtained as a very light gray solid after recrystallization from boiling MeOH. $^1$H NMR (300 MHz, DMSO) δ:9.21 (d, J=4.0 Hz, 1 H), 8.52 (s, 1 H), 8.39 (d, J=8.4 Hz, 1 H), 7.97 (d, J=8.4 Hz, 1 H), 7.83 (m, 2 H), 7.67 (d, J=4.0 Hz, 1 H), 7.56–7.30 (m, 8 H), 6.77 (d, J=2.0 Hz, 1 H), 5.29 (s, 2 H), MP 162–172° C., decomp.

A solution of the benzyl ester (0.12 mmol, 55 mg), palladium black (15 mg) and cyclohexene (1 mL) in 20 mL of MeOH was refluxed for 4.5 h and then filtered through a pad of celite while warm. Addition of methylene chloride to the filtrate produced a fine white powder which was collected on a filter, washed with methylene chloride then dried under reduced pressure (40.5 mg, 91%). $^1$H NMR (300 MHz, DMSO) 9.20 (d, J=4.0 Hz, 1 H), 8.50 (s, 1 H), 8.37 (d, J=8.4 Hz, 1 H), 7.94 (d, J=8.4 Hz, 1 H), 7.82 (brs, 1 H), 7.67 (d, J=8.6 Hz, 2 H), 7.35 (s, 1 H), 7.16 (d, J=2.6 Hz, 1 H), 7.01 (dd, J=8.4, 2.2 Hz, 1 H), 6.77 (d, J=2.1 Hz, 1 H).

Exact Mass. calcd. for $(M+H)^+C_{19}H_{14}ClN_6O_3$: 381.0754, found 381.0767

Employing the synthetic procedure described in Scheme 1 and Scheme 2 the following additional calpain inhibitors were synthesized:

EXAMPLE 14

1,4-Dihydro-1-(2-chloro-4-hydroxyphenyl)-4-oxo-7-(3-chloro-4-pyridazinyl)-3-quinolinecarboxamide

EXAMPLE 15

1.4-Dihydro-1-(2-chloro-4-hydroxyphenyl)-4-oxo-7-phenyl-3-quinolinecarboxamide

EXAMPLE 16

1,4-Dihydro-1-(2,3-dimethyl-4-hydroxyphenyl)-4-oxo-7-(4-pyridyl)-3-quinoline-carboxamide

EXAMPLE 17

1,4-Dihydro-1-(2-chloro-4-benzyloxyphenyl)-4-oxo-7-(2,6-dimethyl-4-pyridyl)-3-quinolinecarboxamide

EXAMPLE 18

1,4-Dihydro-1-(2-chloro-4-hydroxyphenyl)-4-oxo-7-(2,6-dimethyl-4-pyridyl)-3-quinolinecarboxamide

EXAMPLE 19

1,4- Dihydro-1-(2-chloro-4-hydroxyphenyl)-4-oxo-7-(4-pyridyl)-3-quinolinecarboxamide

EXAMPLE 20

1,4-Dihydro-1-(4,hydroxy-2-pyridyl)-4-oxo-7-(2-pyridyl-3-quinolinecarboxamide

EXAMPLE 21

1,4-Dihydro-1-(2-chloro-4-hydroxyphenyl)-4-oxo-7-(4-cyanophenyl)-3-quinolinecarboxamide

EXAMPLE 22

1,4-Dihydro-1-(4-hydroxyphenyl)-4-oxo-7-(4-pyridyl)-3-quinolinecarboxamide

EXAMPLE 23

1,4-Dihydro-1-(2-chloro-4-hydroxphenyl)-4-oxo-7-(2-pyridyl)-3-quinolinecarboxamide

EXAMPLE 24

1,4-Dihydro-1-(2-chloro-4-hydroxyphenyl)-4-oxo-7-(3-fluoro-4-pyridyl)-3-quinolinecarboxamide

EXAMPLE 25

1,4-Dihydro-1-(4-aceamidophenyl)-4-oxo-7-(4-pyridyl)-3-quinolinecarboxamide

EXAMPLE 26

1,4-Dihydro-1-(4-hydroxyphenyl)-4-oxo-7-(4-pyridyl)-3-quinoline-N-methylcarboxamide

EXAMPLE 27

1,4-Dihydro-1-(3-hydroxyphenyl)-4-oxo-7-(4-pyridyl)-3-quinolinecarboxamide

EXAMPLE 28

1,4-Dihydro-1-(4-aminophenyl)-4-oxo-7-(4-pyridyl)-3-quinolinecarboxamide

EXAMPLE 29

1,4-Dihydro-1-(4-carboxyphenyl)-4-oxo-7-(4-pyridyl)-3-quinolinecarboxamide

EXAMPLE 30

1,4-Dihydro-1-(4-carbmethoxyphenyl)-4-oxo-7-(4-pyridyl)-3-quinolinecarboxamide

EXAMPLE 31

1,4-Dihydro-1-(4-trifluoromethylsulfonyloxyphenyl)-4-oxo-7-(4-pyridyl)-3-quinolinecarboxamide

EXAMPLE 32

1,4-Dihydro-1-(4-trifluoroacetamidophenyl)-4-oxo-7-(4-pyridyl)-3-quinolinecarboxamide

EXAMPLE 33

1,4-Dihydro-1-(4-hydroxyphenyl)-4-oxo-7-(4-pyridyl)-3-quinoline-N-hydroxy-carboxamide

EXAMPLE 34

N-(1,4-Dihydro-1-(4-hydroxyphenyl)-4-oxo-7-(4-pyridyl)-3-quinolinoyl)phenylalanine carboxamide

EXAMPLE 35

N-(1,4-Dihydro-1-(4-hydroxyphenyl)-4-oxo-7-(4-pyridyl)-3-quinolinyl)leucine carboxamide

EXAMPLE 36

1,4-Dihydro-1-(4-hydroxyphenyl)-4-oxo-7-bromo-3-quinolinecarboxamide

EXAMPLE 37

1,4-Dihydro-1-(4-hydroxyphenyl)-4-oxo-7-(4-pyridyl)-3-quinoline-N-hydroxyethyl-carboxamide

EXAMPLE 38

1,4-Dihydro-1-(4-hydroxyphenyl)-4-oxo-7-(4-pyridyl)-3-quinoline-N,N-dimethyl-carboxamide

EXAMPLE 39

1.4-Dihydro-1-(4-hydroxyphenyl)-4-oxo-3quinolinecarboxamide

EXAMPLE 40

1,4-Dihydro-1-(4-hydroxyphenyl)4-oxo-7-phenyl-3-quinolinecarboxamide

EXAMPLE 41

1,4-Dihydro-1-(2-chloro-4-hydroxyphenyl)-4-oxo-7-(3,5-dimethyl-4-isoxazolyl)-3-quinolinecarboxamide Compounds of the present invention were tested for calpain I inhibition activity using the following assay method.

Calpain I InhibitionAssay

Isolation of Human erythrocyte Calpain I

Human red blood cells were obtained from the Northeastern New York Chapter of the American Red Cross. The isolation of calpain from human erythrocytes was similar to that described by Wang et al. (1988). One unit of in-dated packed red cells was diluted with an equal volume of diluting/wash solution and centrifuged. The supernatant was removed and the procedure was repeated. The washed cells were pooled, lysed with 700 mL of lysing solution and centrifuged to remove cell debris. The membrane-free hemolysate was added to 500 mL DEAE-sephacel and the slurry was stirred gently at 4° C. for 1 hour.

Batch elution was done using DEAE-sephacel wash solution to remove a large amount of unwanted protein, most of which was hemoglobin. The slurry was poured into a column connected in tandem to a phenyl-sepharose CL-4B column. Material eluted from the DEAE-sephacel was applied directly to the phenyl-sepharose CL-4B. The phenyl-sepharose CL-4B column was washed first with 75 mM NaCl and then with no salt. Calpain begins to disassociate from the DEAE-sephacel with the 75 mM NaCl but the majority should adhere to the column until the salt is removed. Fractions were collected (20 mL), assayed for caseinolytic activity with and without calpastatin and pooled accordingly. The pooled fractions were concentrated using an Amicon stirred cell equipped with a YK-10 membrane. Calpain was stored at 4° C. with 10 mM EDTA and 5 mM 2-mercaptoethanol and is stable for at least 6 months.

Assay Procedure

The tritated assay is a modification of that described by Gopalakrishna, R. and Barsky, S.H., *Anal. Biochem.*, 148, 413,1985. All reagents, compound 25 ul, HEPES buffer 25 ul, CaCl$_2$ 50 ul, enzyme 50 ul, and $^3$H-acetyl Casein, were combined in 1 mL polystyrene titer plates. The plates were preincubated at 25° C. for 5 min with gentle shaking prior to the addition of substrate. The incubation was continued for an additional 2 hours and was terminated with the addition of 0.5 mL ice cold 5% TCA. Unlabled casein was added, samples were centrifuged and 0.5 mL of the supernatant was counted in 5 mL of Ready Protein liquid scintillation cocktail for 2 min. This assay measures $^3$H-acetyl Casein degradation as an endpoint for calpain activity.

Representative assay results are shown in Table 1.

TABLE 1
| Compounds of Example | Structure | IC50 (μM) against human calpain I |
|---|---|---|
| Example 1 | 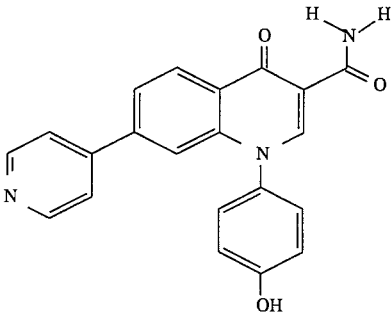 | 2.0 |
| Example 2 | 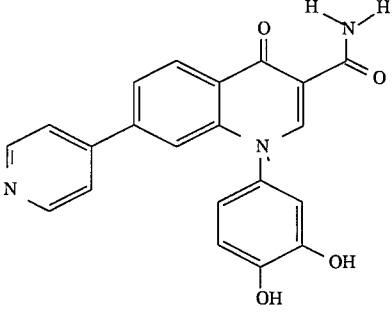 | 7.0 |
| Example 3 | 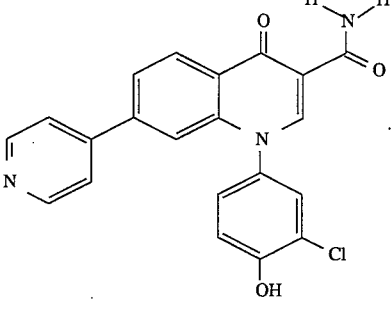 | 2.0 |
| Example 4 | 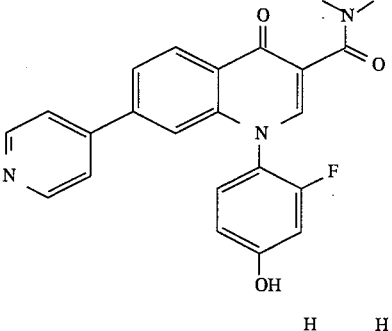 | 7.4 |
| Example 5 | 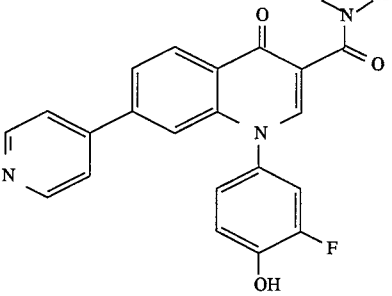 | 5.0 |

TABLE 1-continued

| Compounds of Example | Structure | IC50 (μM) against human calpain I |
|---|---|---|
| Example 6 | (7-(pyridin-4-yl)-4-oxo-1-(2-methyl-4-hydroxyphenyl)quinoline-3-carboxamide) | 0.51 |
| Example 7 | (7-(pyridin-4-yl)-4-oxo-1-(2-trifluoromethyl-4-hydroxyphenyl)quinoline-3-carboxamide) | 16.0 |
| Example 8 | (7-(pyridin-4-yl)-4-oxo-1-(2-chloro-4-hydroxyphenyl)quinoline-3-carboxamide) | 0.6 |
| Example 9 | (7-(pyridin-3-yl)-4-oxo-1-(2-chloro-4-hydroxyphenyl)quinoline-3-carboxamide) | 12.0 |

TABLE 1-continued

| Compounds of Example | Structure | IC50 (μM) against human calpain I |
|---|---|---|
| Example 10 | *(structure)* | 1.7 |
| Example 11 | *(structure)* | 1.7 |
| Example 12 | *(structure)* | 1.7 |
| Example 13 | *(structure)* | 0.57 |

The present invention includes a calpain inhibitor of this invention formulated into compositions together with one or more non-toxic physiologically acceptable carriers, adjuvants or vehicles which are collectively referred to herein as carriers, for parenteral injection or oral administration, in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, ground-nut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated as being within the scope of this invention.

Actual dosage levels of the active ingredient in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the compounds of this invention administered to a host in single or divided doses may be in amounts, for example, of from about 0.5 mg to about 10 mg per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

What is claimed is:

1. A compound of the formula (I)

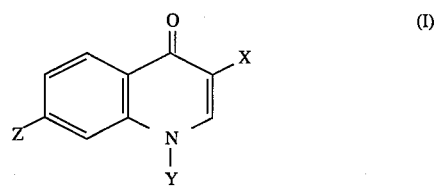

wherein:

Z is aryl, substituted aryl, phenyl-lower-alkyl, hetero-aryl selected from the group consisting of pyrazolyl, imidazolyl, isoxazolyl, tetrazolyl, furyl, thienyl, oxazolyl, thiazolyl, piperidyl, morpholinyl, imidazolinyl, piperazinyl, and thiamorpholinyl, substituted heteroaryl, heterocycloalkyl, heterocyclocalkyl-lower-alkyl, hetero-aryl-lower-alkyl wherein one or more hydrogens of aryl and heteroaryl is optionally replaced by A and B;

Y is phenyl, phenyl-lower-alkyl, wherein one or more hydrogens of phenyl is optionally replaced by A and B;

X is —CONH$_2$, CONHOH, CON(R)$_2$, or CONR—CHR—CO—A or CONR—(CHR)$_n$—A;

A and B are independently H, OH, OR, lower alkyl, N(R)$_2$, CON(R)$_2$, SR, NHSO$_2$R, hydroxy-lower-alkyl, NHCOR, NRSO$_2$CF$_3$, OSO$_2$CF$_3$, or CN;

R is phenyl-lower-alkyl, hydroxy-lower-alkyl, CO-lower-alkyl, or CO—(CH$_2$)$_n$-aryl; and is 1, 2, or 3, a pharmaceutically acceptable salt thereof.

2. A compound having the formula (II)

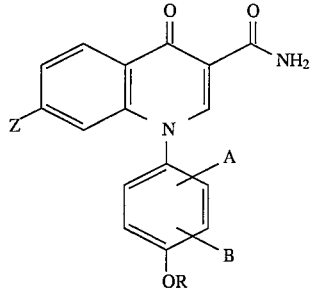

wherein:

Z is aryl, phenyl-lower-alkyl, hetero-aryl selected from the group consisting of, pyrazolyl, imidazolyl, isoxazolyl, tetrazolyl, furyl, thienyl, oxazolyl, thiazolyl, piperidyl, morpholinyl, imidazolinyl, piperazinyl, and thiamorpholinyl, heterocycloalkyl, heterocycloalkyl-lower-alkyl, hetero-aryl-lower-alkyl wherein one or more hydrogens of aryl and heteroaryl is optionally replaced by A and B;

A and B are independently H, OH, OR, lower alkyl, N(R)$_2$, CON(R)$_2$, SR, NHSO$_2$R, hydroxy-lower-alkyl, NHCOR, NRSO$_2$CF$_3$, OSO$_2$CF$_3$, or CN;

R is H, phenyl-lower-alkyl, hydroxy-lower-alkyl, CO-lower-alkyl, or CO—(CH$_2$)$_n$-aryl; and n is 1, 2, or 3, or a pharmaceutically acceptable salt thereof.

3. The compound of claim 1 selected from the group consisting of 1,4-Dihydro-1-(2-chloro-4-hydroxyphenyl)-4-oxo-7-(3-furyl)-3-quinolinecarboxamide, 1,4-Dihydro-1-(2-chloro-4-hydroxyphenyl)-4-oxo-7-(4-pyridazinyl)-3-quinolinecarboxamide, 1,4-Dihydro-1-(2-chloro-4-hydroxyphenyl)-4-oxo-7-(3-pyrazolyl)-3-quinolinecarboxamide, 1,4-Dihydro-1-(2-chloro-4-hydroxyphenyl)-4-oxo-7-(3-chloro-4-pyridazinyl)-3-quinolinecarboxamide, and 1,4-Dihydro-1-(2-chloro-4-hydroxyphenyl)-4-oxo-7-phenyl-3-quinolinecarboxamide.

4. The compound of claim 1 selected from the group consisting of: 1,4-Dihydro-1-(-4-hydroxy-2-pyridyl)-4-oxo-7-(2-pyridyl)-3-quinoline-carboxamide.

5. The compound of claim 1 which is 1,4-Dihydro-1-(4-trifluoromethylsulfonyloxyphenyl)-4-oxo-7-(4-pyridyl)-3-quinolinecarboxamide.

6. The compound of claim 1 selected from the group consisting of: 1,4-Dihydro-1-(4-hydroxyphenyl)-4-oxo-7-bromo-3-quinolinecarboxamide, 1,4-Dihydro-1-(4-hydroxyphenyl)-4-oxo-3-quinolinecarboxamide, 1,4-Dihydro-1-(4-hydroxyphenyl)-4-oxo-7-phenyl-3-quinolinecarboxamide and 1,4-Dihydro-1-(2-chloro-4-hydroxyphenyl)-4-oxo-7-(3,5-dimethyl-4-isoxazolyl)-3-quinolinecarboxamide.

7. A pharmaceutical composition for the treatment or inhibition of ischemia-induced neurodegenerative diseases in a mammal comprising an effective amount of a compound of the formula (I)

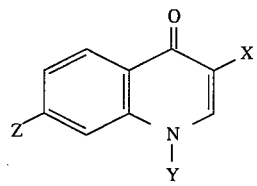

wherein:

Z is aryl, substituted aryl, phenyl-lower-alkyl, hetero-aryl selected from the group consisting of pyrazolyl, imidazolyl, isoxazolyl, tetrazolyl, furyl, thienyl, oxazolyl, thiazolyl, piperidyl, morpholinyl, imidazolinyl, piperazinyl, and thiamorpholinyl, substituted heteroaryl, heterocycloalkyl, heterocyclocalkyl-lower-alkyl, hetero-aryl-lower-alkyl wherein one or more hydrogens of aryl and heteroaryl is optionally replaced by A and B;

Y is phenyl, phenyl-lower-alkyl, wherein one or more hydrogens of phenyl is optionally replaced by A and B;

X is —CONH$_2$, CONHOH, CON(R)$_2$, or CONR—CHR—CO—A or CONR—(CHR)$_n$—A;

A and B are independently H, OH, OR, lower alkyl, N(R)$_2$, CON(R)$_2$, SR, NHSO$_2$R, hydroxy-lower-alkyl, NHCOR, NRSO$_2$CF$_3$, OSO$_2$CF$_3$, or CN;

R is phenyl-lower-alkyl, hydroxy-lower-alkyl, CO-lower-alkyl, or CO—(CH$_2$)$_n$-aryl; and n is 1, 2, or 3, or a pharmaceutically acceptable salt thereof.

8. The pharmaceutical composition for the treatment or inhibition of ischemia-induced neurodegenerative diseases in a mammal comprising an effective amount of a compound of the formula (II)

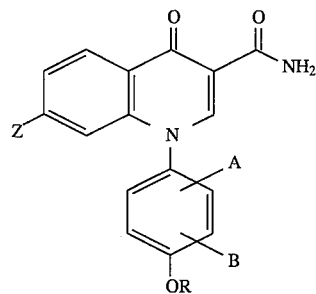

wherein:

Z is aryl, phenyl-lower-alkyl, hetero-aryl selected from the group consisting of pyrazolyl, imidazolyl, isoxazolyl, tetrazolyl, furyl, thienyl, oxazolyl, thiazolyl, piperidyl, morpholinyl, imidazolinyl, piperazinyl, and thiamorpholinyl, heterocycloalkyl, heterocycloalkyl-lower-alkyl, hetero-aryl-lower-alkyl wherein one or more hydrogens of aryl and heteroaryl is optionally replaced by A and B;

A and B are independently H, OH, OR, lower alkyl, N(R)$_2$, CON(R)$_2$, SR, NHSO$_2$R, hydroxy-lower-alkyl, NHCOR, NRSO$_2$CF$_3$, OSO$_2$CF$_3$, or CN;

R is H, phenyl-lower-alkyl, hydroxy-lower-alkyl, CO-lower-alkyl, or CO—(CH$_2$)$_n$-aryl; and n is 1, 2, or 3, or a pharmaceutically acceptable salt thereof.

9. A pharmaceutical composition for the treatment or inhibition of ischemia-induced neurodegenerative disease wherein said compound is selected from the group consisting of: 1,4-Dihydro-1-(2-chloro-4-hydroxyphenyl)-4-oxo-7-(4-pyridazinyl)-3-quinolinecarboxamide, 1,4-Dihydro-1-(2- chloro-4-hydroxyphenyl)-4-oxo-7-(3-pyrazolyl)-3-quinolinecarboxamide, 1,4-Dihydro-1-(2-chloro-4-hydroxyphenyl)-4-oxo-7-(3-pyrazolyl)-3-quinolinecarboxamide, 1,4-Dihydro-1-(2-chloro-4-hydroxyphenyl)-4-oxo-7-(3-chloro-4-pyridazinyl)-3-quinolinecarboxamide, and 1,4-Dihydro-1-(2-chloro-4-hydroxyphenyl)-4-oxo-7-phenyl-3-quinolinecarboxamide.

10. A pharmaceutical composition for the treatment or inhibition of ischemia-induced neurodegenerative disease wherein said compound is 1,4-Dihydro-1-(4-trifluoromethylsulfonyloxyphenyl)-4-oxo-7-(4-pyridyl)-3-quinolinecarboxamide.

11. The pharmaceutical composition of claim 7 wherein said compound is selected from the group consisting of: 1,4-Dihydro-1-(4-hydroxyphenyl)-4-oxo-3quinolinecarboxamide, 1,4-Dihydro-1-(4-hydroxyphenyl)-4-oxo-7-phenyl-3quinolinecarboxamide and 1,4-Dihydro-1-(2-chloro-4-hydroxyphenyl)-4-oxo-7-(3,5-dimethyl-4-isoxazolyl)-3-quinolinecarboxamide.

12. A method of treating or inhibiting ischemia-induced neurodegenerative disease in a mammal comprising the administration to said mammal an effective amount of a composition according to claim 7.

13. A method of treating or inhibiting ischemia-induced neurodegenerative disease in a mammal comprising the administration to said mammal an effective amount of a composition according to claim 8.

14. A method of treating or inhibiting ischemia-induced neurodegenerative disease in a mammal comprising the administration to said mammal an effective amount of a composition according to claim 9.

15. A method of treating or inhibiting ischemia-induced neurodegenerative disease in a mammal comprising the administration to said mammal an effective amount of a composition according to claim 10.

16. A method of treating or inhibiting ischemia-induced neurodegenerative disease in a mammal comprising the administration to said mammal an effective amount of a composition according to claim 11.

* * * * *